United States Patent
Baba et al.

(10) Patent No.: US 8,523,776 B2
(45) Date of Patent: Sep. 3, 2013

(54) ULTRASONIC DOPPLER IMAGING APPARATUS AND METHOD WITH BLOOD VELOCITY WAVEFORM PROCESSING

(75) Inventors: Tatsuro Baba, Otawara (JP); Muneki Kataguchi, Nasushiobara (JP); Kazuya Akaki, Nasushiobara (JP); Shuichi Kawasaki, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1139 days.

(21) Appl. No.: 12/140,607

(22) Filed: Jun. 17, 2008

(65) Prior Publication Data
US 2009/0024037 A1  Jan. 22, 2009

(30) Foreign Application Priority Data
Jul. 17, 2007 (JP) ................ 2007-185882

(51) Int. Cl.
*A61B 8/06* (2006.01)

(52) U.S. Cl.
USPC ........... 600/454; 600/453; 600/455; 600/456; 600/457

(58) Field of Classification Search
None
See application file for complete search history.

(56) References Cited

U.S. PATENT DOCUMENTS

| | | | |
|---|---|---|---|
| 5,634,465 A * | 6/1997 | Schmiesing et al. | 600/454 |
| 6,024,701 A * | 2/2000 | Almog | 600/300 |
| 6,050,948 A * | 4/2000 | Sasaki et al. | 600/453 |
| 6,293,913 B1 * | 9/2001 | Tsujino et al. | 600/450 |
| 6,340,346 B1 * | 1/2002 | Almog et al. | 600/300 |
| 6,733,454 B1 * | 5/2004 | Bakircioglu et al. | 600/453 |
| 2005/0080329 A1 * | 4/2005 | Uchibori | 600/407 |
| 2006/0052704 A1 | 3/2006 | Baba et al. | |
| 2006/0084873 A1 | 4/2006 | Baba et al. | |

FOREIGN PATENT DOCUMENTS

JP 2005-185731 7/2005

OTHER PUBLICATIONS

U.S. Appl. No. 12/238,829, filed Sep. 26, 2008, Baba, et al.

* cited by examiner

*Primary Examiner* — Long V. Le
*Assistant Examiner* — Bradley Impink
(74) *Attorney, Agent, or Firm* — Oblon, Spivak, McClelland, Maier & Neustadt, L.L.P.

(57) ABSTRACT

Transmitting and receiving ultrasound with repetition frequency that corresponds to velocity range indicating the measurable velocity to and from a diagnostic site that contains moving fluid within a body to be examined. Generating Doppler spectrum image showing velocity of moving fluid based on signals obtained from transmission and reception of ultrasound. Storing modeled value based on model correlating standard blood velocity waveform with an ECG waveform. Calculating measured blood velocity waveform based on spectrum image of a specified patient. Acquiring ECG waveform at timing corresponding to measured blood velocity waveform. Estimating blood velocity waveform excluding effects of valve signals of patient based on measured blood velocity waveform, ECG waveform, and modeled value. Comparing measured blood velocity waveform with estimated blood velocity waveform, to exclude excess parts of the difference over a threshold from measured blood velocity waveform, and to interpolate excluded parts of measured blood velocity waveform.

7 Claims, 6 Drawing Sheets

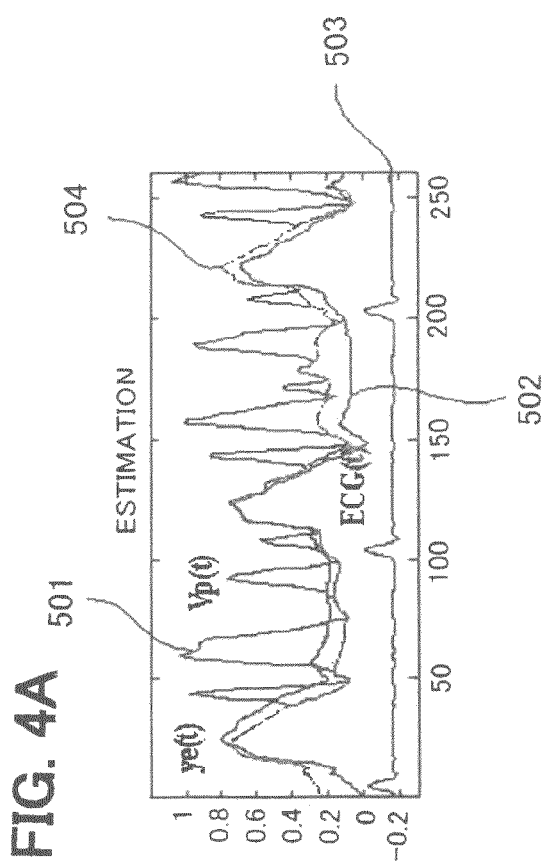
FIG. 4A
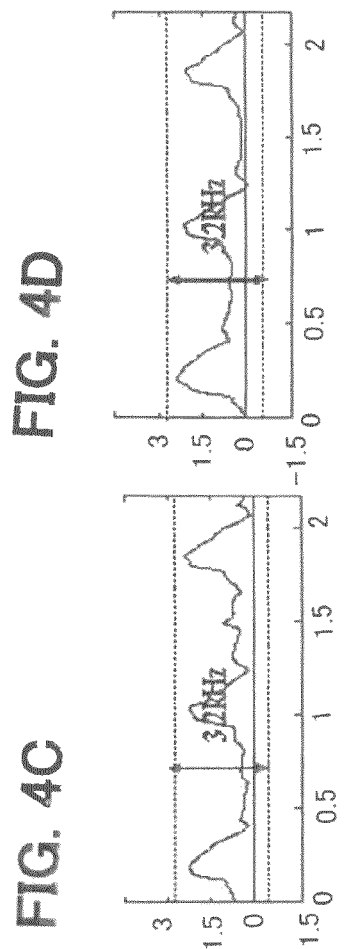
FIG. 4D
FIG. 4C
FIG. 4B

ULTRASONIC DOPPLER IMAGING APPARATUS AND METHOD WITH BLOOD VELOCITY WAVEFORM PROCESSING

BACKGROUND OF THE INVENTION

1. Field of the Invention

The present invention relates to an ultrasonic imaging apparatus and a method of acquiring ultrasonic images for generating a Doppler spectrum image. Specifically, it relates to an ultrasonic imaging apparatus and a method of acquiring ultrasonic images that automatically adjust the velocity range of a Doppler spectrum image.

2. Description of the Related Art

Conventionally known ultrasonic imaging apparatuses concomitantly adopt an ultrasonic pulse reflection method and an ultrasonic Doppler method, in order to obtain cross-sectional images of diagnostic sites and the bloodstream information thereof through ultrasonic manipulation using one ultrasonic probe to display at least the bloodstream information in real time. These ultrasonic imaging apparatuses are used for analyzing the Doppler shift frequency based on the principle of the ultrasonic Doppler method, to obtain bloodstream information from the results of the analysis, the principle of the ultrasonic Doppler method meaning that the received frequency shifts slightly from the transmitted frequency due to the Doppler effect of the ultrasound transmitted to and received at a diagnostic site having a flow such as that of blood in a body, so that the shift frequency (Doppler shift frequency) is proportional to the blood velocity.

In the above-mentioned ultrasonic imaging apparatuses, items (parameters) to be used for a diagnosis are measured for a spectrum image of a Doppler frequency that displays the results of a frequency analysis with the Fast Fourier Transform (FFT) of an obtained Doppler signal in spectrum display with the frequency as the vertical axis, time t as the a horizontal axis, and power (strength) of frequency components as luminance (tone).

The operational flow of this measurement process is described in sequence. (1) On a spectrum image of a Doppler frequency, positions of a maximum flow velocity Vp (V peak) that corresponds to the maximum frequency and a mean velocity Vm (V mean) that corresponds to the mean frequency within a frequency distribution in the axial direction of the frequency are calculated.

(2) Each change in time of the maximum flow velocity Vp and mean flow velocity Vm is traced in the axial direction of the time. (3) On a trace waveform that shows curves of temporal positional changes of the Vp and Vm, a systolic waveform peak PS (Peak of Systolic) and a diastolic waveform peak ED (End of Diastolic) are simultaneously detected during each cardiac cycle (1 heartbeat). (4) Based on information of the PS and ED, various parameters (indexes) for a diagnosis such as an intravascular blood flow volume, HR (Heart Rate) of pulsatile flow, PI (Pulsatility Index), and RI (Resistance Index), etc. are measured, and a process to display those measurements (parameter measurement process) is conducted.

The above-mentioned trace waveform detection processes for Vp and Vm, peak detection processes for PS and ED, and parameter measurement processes such as PI and RI, etc. are basically conducted through manual operation using a freeze image. Moreover, in recent years, ultrasonic imaging apparatuses that conduct the same processes with automatic operation using real-time images have also been widely used.

In the Pulse Doppler (PW) method, a pulse with a predetermined repetition frequency is transmitted and the frequency of the received signal is analyzed with a predetermined sampling frequency. When the sampling frequency fs for this frequency analysis is lower than the Doppler shift frequency, aliasing (folding) occurs. Therefore, to prevent this, it is necessary to increase the pulse repetition frequency (PRF) and shorten the intervals between each observation time. In this case, designating a location to be measured consequently decides the maximum PRF, and once the PRF is decided, the measurable maximum blood velocity is also decided.

This measurable maximum blood velocity is called the velocity range.

For example, to measure the velocity of blood flow that is approximately 30 cm/s, if a velocity range of approximately 10 cm is set, aliasing occurs and the blood flow cannot be measured. Thus, in this case, it is necessary to set the velocity range at approximately 50 cm/s.

With a Doppler spectrum display, when the velocity range is too small, a folding portion is generated as described above. In such a case, an operator can manually set the Doppler velocity range at a higher value, by which the folding portion falls within the Nyquist rate (half of the PRF) and a Doppler spectrum image that is smooth on the display can be obtained.

In contrast, when the velocity range is too large, the waveform of a spectrum becomes small, causing difficulty in observation. In such a case, an operator can obtain a Doppler spectrum image that efficiently uses the top and bottom portions of the display screen and is easy to observe by setting the velocity range to a low value.

Moreover, in the ultrasonic Doppler method, a positive sign is assigned to blood flow that goes toward the ultrasonic probe in the direction of blood flow. Moreover, a negative sign is assigned to blood flow that goes away from the probe. When an ultrasonic probe is applied to a specific vessel and the vessel is an artery, the velocity of the blood flow changes depending on heartbeat but does not change between positive and negative, usually placing a disproportionate emphasis on either positive or negative.

For example, with Doppler spectrum display, when a folding portion occurs, an operator may shift the baseline (BL=0) of the Doppler spectrum image by manipulating the baseline shift switch. This is called an adjustment of velocity offset. By shifting this baseline by only −0.25 (amount of baseline shift=−0.25), the folding portion moves beyond the Nyquist rate and a Doppler spectrum that is smooth on the display can be obtained.

A Doppler spectrum image that is obtained with an ultrasonic imaging apparatus will now be described with reference to FIG. 1. FIG. 1 is a diagram that shows cross-sectional images and Doppler spectrum images acquired by means of an ultrasonic imaging apparatus. A case in which cross-sectional images and Doppler spectrum images are acquired and displayed with a carotid artery as the diagnostic site will now be described.

For example, in a screen 110, when a vessel shown in an image in which a B-mode cross-sectional image 100 and a color Doppler image 101 are superimposed is designated by a range gate 102, which is used to designate the location at which a Doppler spectrum image is acquired, a Doppler spectrum image that shows the time change of the blood velocity distribution at that location is obtained and displayed on the screen. On a screen 111, a Doppler spectrum image 103 with a PRF for determining the velocity range (measurable maximum blood velocity) of 7.1 (kHz) and a velocity offset (BLS: Baseline Shift) of 0 (Hz) is shown (part indicated with a dotted line in the screen 110).

Furthermore, for measurement of the state of blood flow based on the shape of the peak determined through an auto trace of the Doppler spectrum image 103, an operator adjusts the pulse repetition frequency (PRF) and velocity offset (BLS) in a screen 120 so that the state of the blood flow is displayed with a specific ratio in the center of the velocity range (vertical axis). For example, by changing the PRF to 5 (kHz) and shifting the BLS to the negative side, the Doppler spectrum image 103 is enlarged and displayed as shown in screen 121 (part indicated with a dotted line in the screen 120).

When measuring the blood velocity, etc. with an ultrasonic imaging apparatus, the blood velocity that is measured changes largely depending on any disorders and the physical condition of the subject, how the probe is applied (angle), the location and width of the intravascular range gate with a PW Doppler, and the diagnostic site. Therefore, conventionally, an operator has performed optimization each time by adjusting the velocity range of the apparatus and shifting the baseline to measure HR, PI, and RI from an enlarged waveform. However, it is cumbersome to adjust the PRF and velocity offset (BLS) to correspond to the velocity range each time the state of blood flow to be diagnosed changes.

Therefore, ultrasonic imaging apparatuses that provide automatic operation for adjustments of the velocity range and velocity offset of a Doppler spectrum image and improved operability of blood flow measurement so that an operator does not need to pay attention to the setup of the apparatus have been proposed (for example, Japanese published unexamined application No. 2005-185731). According to a technique related to the conventional art, a histogram that shows the frequency distribution of a velocity is created by calculating the frequency of a maximum velocity (frequency) based on a Doppler waveform acquired at a predetermined timing (for example, 1 heartbeat), and based on the histogram, the velocity range is determined so that the Doppler waveform is displayed within α% (for example, 70%) of the vertical direction of the display area, and feedback is given.

At this time, to automatically adjust the velocity range of a Doppler spectrum image, stability and reliability during the measurement of a Doppler spectrum are important issues. However, the circulatory organs (heart) have valves to circulate blood, etc., and therefore signals (hereinafter referred to as "valve signals") are generated when the valves operate. Therefore, with a conventional ultrasonic imaging apparatus, it was difficult to automatically adjust the velocity range for only a blood flow component, particularly for Doppler blood flow diagnoses of a circulatory organ (heart), because valve signals with high power are incorporated along with blood flow signals.

SUMMARY OF THE INVENTION

The present invention purposes to provide an ultrasonic imaging apparatus that estimates a waveform that corresponds to an intended cardiac phase and is not affected by the waveforms of valve signals, that automatically excludes any areas incorporating valve signals in a cardiac phase from a measured blood velocity waveform based on the estimated waveform, and that creates a measured blood flow waveform with the effects of the valve signals excluded by interpolating the excluded parts.

Moreover, it purposes to provide an ultrasonic imaging apparatus that automatically excludes any area that incorporates valve signals in a cardiac phase from a measured blood velocity waveform based on an estimated waveform, and that automatically adjusts the velocity range based on the measured blood velocity waveform with the valve signals excluded.

An ultrasonic imaging apparatus of the first aspect of this invention comprises a transceiving part, a Doppler signal-processing part, a memory part, a measured waveform calculation part, an ECG waveform acquisition part, a waveform estimation part, and an interpolation part. Moreover, the transceiving part transmits and receives ultrasound with a repetition frequency that corresponds to a velocity range indicating the measurable velocity to and from a diagnostic site that contains a moving fluid within the body to be examined. The Doppler signal-processing part generates a Doppler spectrum image that shows the velocity of the moving fluid based on signals obtained from the transmission and reception of the ultrasound. The memory part preliminarily stores values that have been modeled based on a model that correlates the standard blood velocity waveform with the ECG waveform. The measured waveform calculation part calculates the measured blood velocity waveform based on the spectrum image of a specified patient. The ECG waveform acquisition part acquires the ECG waveform at a timing corresponding to the measured blood velocity waveform. The waveform estimation part estimates the blood velocity waveform while excluding the effects of valve signals of the patient based on the measured blood velocity waveform, the ECG waveform, and the modeled value. The interpolation part compares the measured blood velocity waveform with the estimated blood velocity waveform, excludes excess parts of the difference over a threshold from the measured blood velocity waveform, and interpolates the excluded parts of the measured blood velocity waveform.

According to this first aspect, a blood velocity waveform with the effects of valve signals excluded can be generated automatically. Through this, a Doppler spectrum image that is not affected by valve signals and that is easy to trace can be generated, enabling the improvement of measurement accuracy of blood flow volume, etc.

Moreover, an ultrasonic imaging apparatus of the second aspect of this invention comprises a transceiving part, a Doppler signal-processing part, a memory part, a measured waveform calculation part, an ECG waveform acquisition part, a waveform estimation part, and a velocity range setup part. Moreover, the transceiving part transmits and receives ultrasound with a repetition frequency that corresponds to a velocity range indicating the measurable velocity to and from a diagnostic site that contains a moving fluid within the body to be examined. The Doppler signal-processing part generates a Doppler spectrum image that shows the velocity of the moving fluid based on signals obtained from the transmission and reception of the ultrasound. The memory part preliminarily stores values that have been modeled based on a model that correlates the standard blood velocity waveform with the ECG waveform. The measured waveform calculation part calculates the measured blood velocity waveform based on the spectrum image of a specified patient. The ECG waveform acquisition part acquires the ECG waveform at a timing corresponding to the measured blood velocity waveform. The waveform estimation part estimates the blood velocity waveform excluding the effects of valve signals of the patient based on the measured blood velocity waveform, the ECG waveform, and the modeled value. The velocity range setup part compares the measured blood velocity waveform with the estimated blood velocity waveform and calculates the velocity range based on the measured blood velocity waveform while excluding excess parts of the difference over a threshold.

According to this second aspect, an optimum velocity range that corresponds to a blood velocity waveform with the effects of valve signals excluded can be calculated automatically. Thereby, a Doppler spectrum image that is easy for an operator to read can be generated.

An ultrasonic imaging apparatus of the third aspect of this invention comprises a transceiving part, a Doppler signal-processing part, a memory part, and an abnormality determination part. Moreover, the transceiving part transmits and receives ultrasound with a repetition frequency based on a velocity range indicating the measurable velocity to and from a diagnostic site that contains a moving fluid within the body to be examined. The Doppler signal-processing part generates a Doppler spectrum image that shows the velocity of the moving fluid based on signals obtained from the transmission and reception of the ultrasound. The memory part preliminarily stores values that have been modeled on a model of a commonly used standard blood velocity waveform based on statistical data of an individual ECG waveform and a corresponding standard blood velocity waveform. The abnormality determination part creates a state space, which is an area that includes a blood velocity waveform that can be considered as a normal state based on statistical data of the individual ideal blood velocity waveform, and it determines that a blood velocity is abnormal when the Mahalanobis' distance of the measured bloodstream information from the state space exceeds a predetermined threshold.

According to this third aspect, any abnormality in blood velocity can be determined automatically. Thereby, oversights of abnormalities in blood velocity can be reduced and abnormalities can be detected at an early stage.

The fourth aspect of this invention is a method of acquiring ultrasonic images comprising: a transceiving step that transmits and receives ultrasound with a repetition frequency that corresponds to a velocity range indicating the measurable velocity to and from a diagnostic site that contains a moving fluid within the body to be examined; a Doppler signal-processing step that generates a Doppler spectrum image that shows the velocity of the moving fluid based on signals obtained from the transmission and reception of the ultrasound, a memory step that preliminarily stores values that have been modeled based on a model that correlates the standard blood velocity waveform with the ECG waveform; a measured waveform calculation step that calculates the measured blood velocity waveform based on the spectrum image of a specified patient; an ECG waveform acquisition step that acquires the ECG waveform at a timing corresponding to the measured blood velocity waveform; a waveform estimation step that estimates the blood velocity waveform of the patient based on the measured blood velocity waveform, the ECG waveform, and the modeled value; and an interpolation step that compares the measured blood velocity waveform with the estimated blood velocity waveform, excludes excess parts of the difference over a threshold from the measured blood velocity waveform, and interpolates the excluded parts of the measured blood velocity waveform.

The fifth aspect of this invention is a method of acquiring ultrasonic images comprising: a transceiving step that transmits and receives ultrasound with a repetition frequency that corresponds to a velocity range indicating the measurable velocity to and from a diagnostic site that contains a moving fluid within the body to be examined; a Doppler signal-processing step that generates a Doppler spectrum image that shows the velocity of the moving fluid based on signals obtained from the transmission and reception of the ultrasound; a memory step that preliminarily stores values that have been modeled based on a model that correlates the standard blood velocity waveform with the ECG waveform; a measured waveform calculation step that calculates the measured blood velocity waveform based on the spectrum image of a specified patient; an ECG waveform acquisition step that acquires the ECG waveform at a timing corresponding to the measured blood velocity waveform; a waveform estimation step that estimates the blood velocity waveform of the patient based on the measured blood velocity waveform, the ECG waveform, and the modeled value; and a velocity range setup step that compares the measured blood velocity waveform with the estimated blood velocity waveform and calculates the velocity range based on the measured blood velocity waveform while excluding excess parts of the difference over a threshold.

BRIEF DESCRIPTION OF THE DRAWINGS

FIG. 4A is a diagram of a graph for calculating a blood velocity waveform using an ultrasonic imaging apparatus related to the present invention; FIG. 4B is a diagram of a graph when the velocity range of the collective waveforms was set up manually in a conventional ultrasonic imaging apparatus; FIG. 4C is a diagram of a graph that shows an ideal velocity range of an example blood velocity waveform; and FIG. 4D is a diagram of a graph when the velocity range of a blood velocity waveform was set up using an ultrasonic imaging apparatus related to Embodiment 1.

DETAILED DESCRIPTION OF THE EMBODIMENTS

[Embodiment 1]

Figure 1:
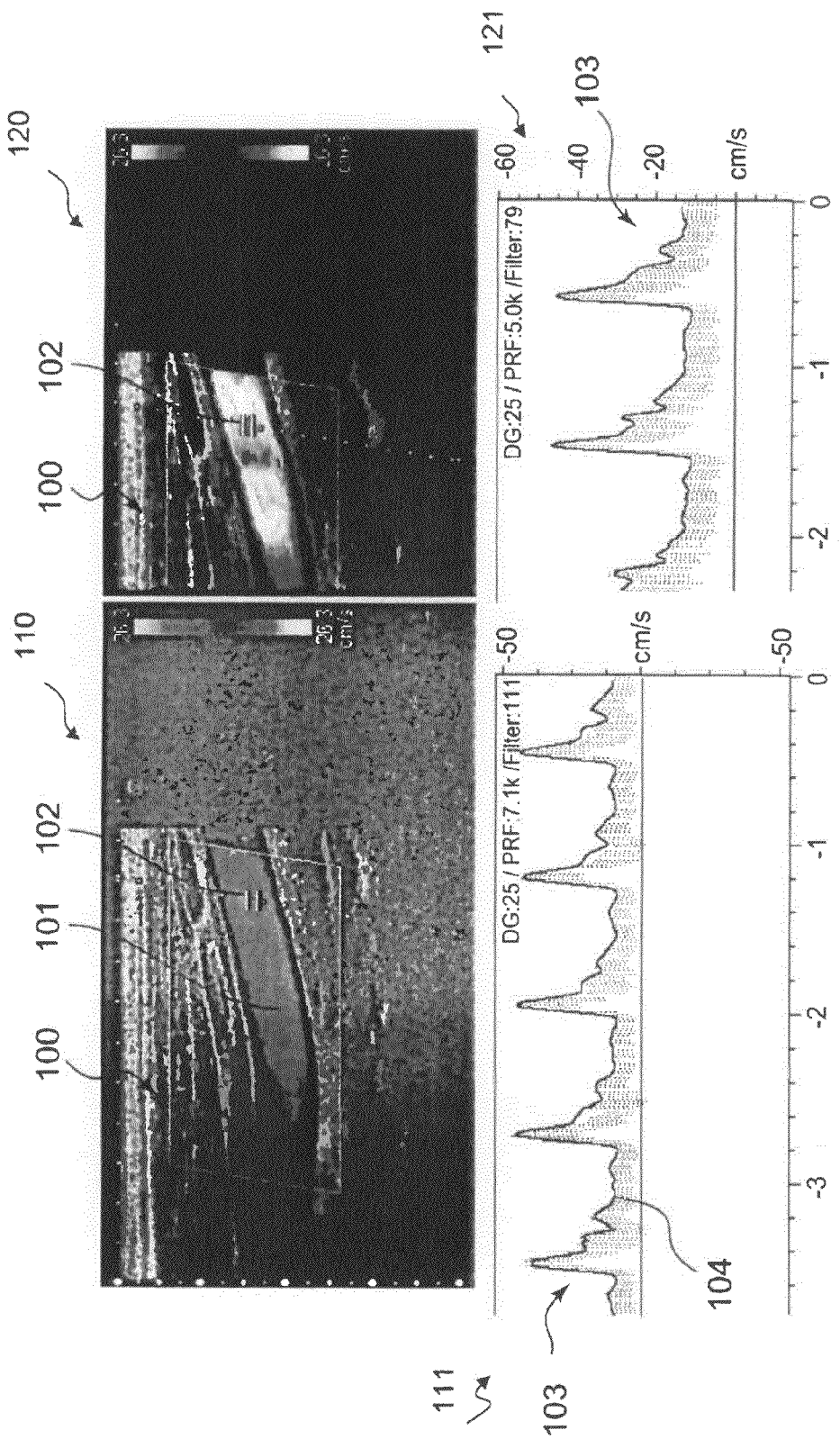
FIG. 1 is a diagram that shows cross-sectional images and Doppler spectrum images acquired with an ultrasonic imaging apparatus.
Figure 2:
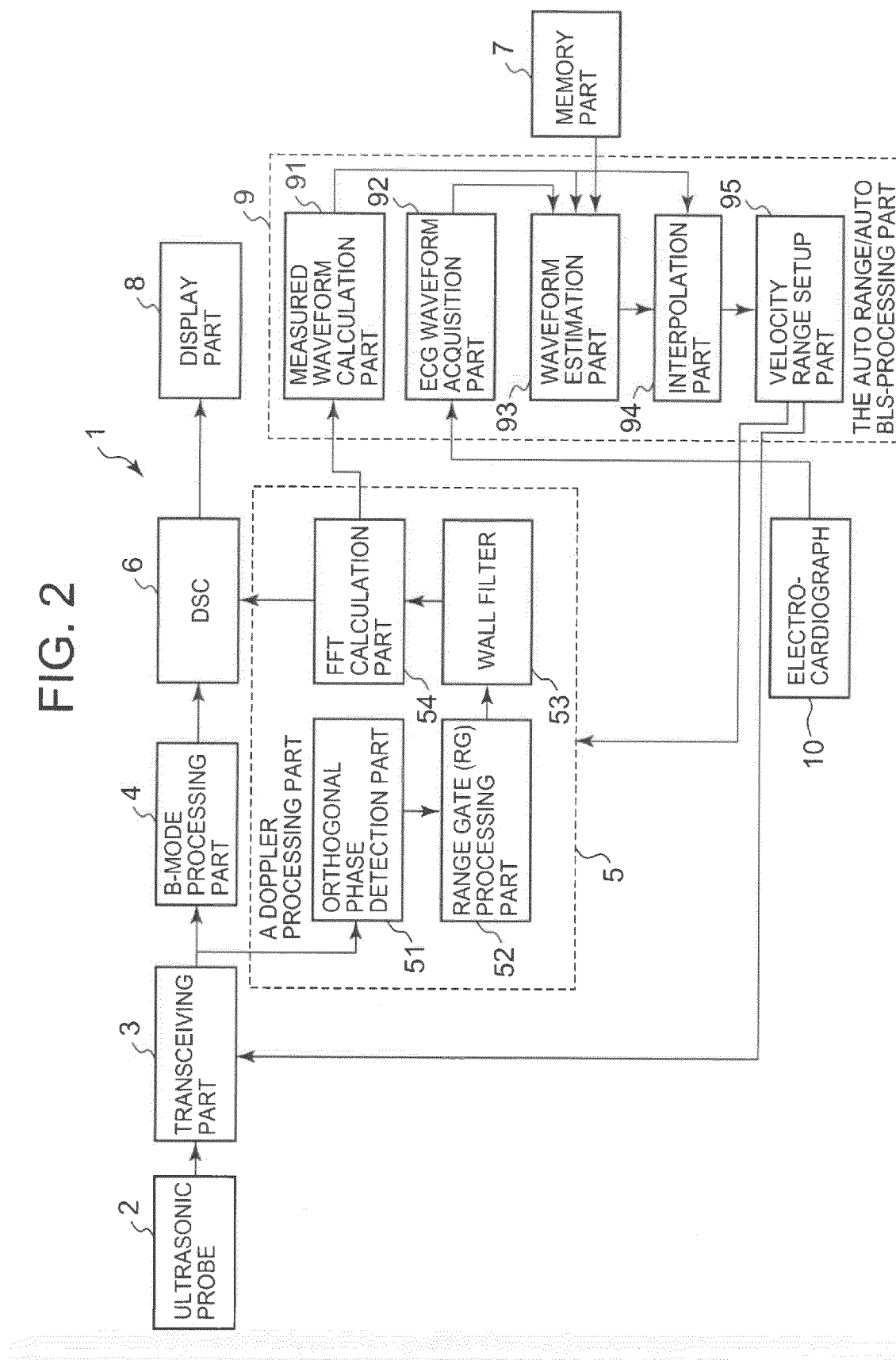
FIG. 2 is a block diagram of an ultrasonic imaging apparatus related to Embodiment 1.

An ultrasonic imaging apparatus and a method of processing ultrasonic images related to Embodiment 1 of this invention will now be described. FIG. 2 is a block diagram that shows a skeleton framework of the ultrasonic imaging apparatus related to Embodiment 1 of the present invention.

The ultrasonic imaging apparatus 1 related to Embodiment 1 is operable according to known modes such as a B-mode that displays an ultrasonic cross-sectional image (B-mode cross-sectional image), a Doppler mode (pulse Doppler (PW) or continuous Doppler (CW)) that displays bloodstream information, and a CFM (Color Flow Mapping) mode that 2-dimensionally displays bloodstream information, etc.

For an ultrasonic probe 2, a 1-dimensional ultrasonic probe with a plurality of ultrasonic transducers aligned in one line in a predetermined direction (scanning direction) and a 2-dimensional ultrasonic probe with ultrasonic transducers arranged in a matrix are used.

A transceiving part 3 comprises a transmission part (not shown) that supplies electrical signals to the ultrasonic probe 2 to generate ultrasound and a receiving part (not shown) that receives signals from the ultrasonic probe 2.

The transmission part of the transceiving part 3 comprises a clock generation circuit, a transmission delay circuit, and a pulsar circuit, which are not shown. The clock generation circuit is a circuit that generates a clock signal that decides the transmission timing and the transmitted frequency of an ultrasonic signal. The transmission delay circuit is a circuit that conducts transmission focus by introducing a delay when ultrasound is transmitted. The pulsar circuit incorporates a pulsar for a few minutes for each individual route that corresponds to each ultrasonic transducer, generates a drive pulse at the transmission timing with the delay, and supplies each ultrasonic transducer of the ultrasonic probe 2.

Moreover, the receiving part of the transceiving part 3 comprises a pre-amp circuit, an A/D conversion circuit, and a reception delay/adder circuit, which are not shown. The pre-amp circuit amplifies any echo signal that is output from each ultrasonic transducer of the ultrasonic probe 2 for each receiving channel. The A/D conversion circuit conducts A/D conversion of the amplified echo signals. The reception delay/adder circuit provides the delay time necessary to decide the receiving directionality for the echo signals after A/D conversion and adds it. The addition emphasizes the reflected components from the direction according to the receiving directionality. Additionally, signals that have been processed for addition by this transceiving part 3 are called "RF signals." The RF signals output from the transceiving part 3 are output to a B-mode processing part 4 or a Doppler processing part 5. Furthermore, when the transceiving part 3 receives a repetition frequency (PRF) from a velocity range setup part 95, it causes the ultrasonic probe 2 to transmit and receive ultrasound according to the repetition frequency.

The B-mode processing part 4 visualizes the amplitude information of the echo and generates B-mode ultrasonic raster data from the echo signals. Specifically, a B-mode processing circuit conducts a band pass filter process of the RF signals and then detects the envelope curve of the output signals and conducts a compression process using logarithmic conversion of the detected data. The B-mode ultrasonic raster data generated by the B-mode processing part 4 is output to a DSC 6.

The Doppler processing part 5 comprises an orthogonal phase detection part 51, a range gate (RG) processing part 52, a wall filter 53, and an FFT calculation part 54.

The quadrature detection part 51 incorporates a reference signal from a reference transmitter and a reference signal with a phase difference of 90 degrees with the RF signals output from the transceiving part 3. The range gate (RG) processing part 52 excludes any high-frequency components from the incorporated signals to obtain Doppler signals that consist of only Doppler shift frequency components and subsequently extracts Doppler signals from an intended depth in the body to be examined. The wall filter 53 excludes any unnecessary low-frequency Doppler signals that are relatively slow in motion, such as signals from vascular walls and cardiac walls, etc. from the Doppler signals in the body to be examined designated by the range gate from the range gate processing part 52 and extracts Doppler signals of the blood flow to be detected. The FFT calculation part 54 conducts a frequency analysis of the Doppler signals extracted by the wall filter 53, obtains the Doppler spectrum signals, which are the analytical results, and outputs to the DSC (Digital Scan Converter) 6. Thereby, a Doppler spectrum image is displayed on a display part 8 along with a B-mode cross-sectional image, for example.

Moreover, when the FFT calculation part 54 receives a velocity offset (BLS) from the velocity range setup part 95, it changes only the read address of the FFT process for the displacement and adjusts the offset of the velocity.

The DSC 6 converts the ultrasonic raster data into image data that is shown in orthogonal coordinates in order to obtain an image that is shown in an orthogonal coordinate system (Scan Conversion process). The image data is output from the DSC 6 to the display part 8, and an image based on the image data is displayed on the display part 8. For example, the DSC 6 generates cross-sectional image data as 2-dimensional information based on the B-mode ultrasonic raster data and outputs the cross-sectional image data to the display part 8. The display part 8 displays a cross-sectional image based on the cross-sectional image data.

An auto range/auto BLS-processing part 9 receives the Doppler spectrum signals output from the FFT calculation part 54 and calculates the optimum velocity range for the Doppler spectrum signals. The auto range/auto BLS-processing part 9 comprises a measured waveform calculation part 91, an ECG waveform acquisition part 92, a waveform estimation part 93, an interpolation part 94, and a velocity range setup part 95. The auto range/auto BLS-processing part 9 is described in detail below.

The measured waveform calculation part 91 detects the measured blood velocity waveform of the Vp (hereinafter referred to as "trace") by detecting the maximum velocity Vp of the Doppler spectrum signals output from the FFT calculation part 54 and connecting in the direction of that time (for example, the detecting phase or pseudo filtering may be used). Thereby, the measured blood velocity waveform of the maximum velocity Vp becomes a waveform that has traced the maximum velocity Vp of the Doppler spectrum image. Subsequently, the measured waveform calculation part 91 calculates a function Vp(t) that indicates the measured blood velocity waveform (hereinafter referred to as "measured blood velocity waveform Vp(t)") from the detected measured blood velocity waveform. Furthermore, the measured waveform calculation part 91 transmits the measured blood velocity waveform Vp(t) to the waveform estimation part 93 and the interpolation part 94.

The ECG waveform acquisition part 92 receives a signal from an electrocardiograph 10, synchronizes the signal with the measured blood velocity waveform calculated by the measured waveform calculation part 91, and traces the maximum amplitude in the direction of that time to create an ECG waveform. Furthermore, based on the created ECG waveform, the ECG waveform acquisition part 92 creates a function u(t) that indicates the ECG waveform (hereinafter referred to as "ECG waveform u(t)"). Subsequently, the ECG waveform acquisition part 92 transmits the created ECG waveform u(t) to the waveform estimation part 93.

Based on pre-collected statistical data of the ECG waveform of an individual patient for each age and disorder and an ideal blood velocity waveform of a corresponding individual patient with no effects of valve signals, a memory part 7 conducts system identification using an ARX model (Auto-Regressive exogenous model) in order to model it into a model of a commonly used ideal blood velocity waveform and preliminarily stores a coefficient series of the model. This ideal blood velocity waveform with no effects of valve signals is the "standard blood velocity waveform" in the present invention. Here, the ARX model is a linear time-variant parametric model that is used for system identification and correlates a present output y(t) with limited past output data y(t−k) and input data u(t−k) (for example, refer to "system identification by MATLAB" by Shuichi Adachi, Tokyo Denki University Press).

The method of calculating the above mentioned coefficient series will now be described. Firstly, ages and disorders are classified into groups, and several hundred cases of ECG (Electrocardiogram) waveforms and ideal blood velocity waveforms with no effects of valve signals are collected for each group. At this time, as a method of obtaining an ideal blood velocity waveform, a blood velocity waveform with no effects of valve signals is obtained by measuring the blood velocity at a part with no reciprocal valves in the circulatory organ. Alternatively, for this purpose, a blood velocity waveform with no effects of valve signals is obtained by a physician with experience by manually eliminating the effects of valve signals from a measured blood velocity waveform based on their experience.

Next, based on the collected ECG waveform and ideal blood velocity waveform, system identification using the ARX model is conducted. This is expressed with the following function, in which u(t) indicates an ECG waveform and yi(t) indicates a commonly used ideal blood velocity waveform.

$$A(q)*yi(t)=B(q)*u(t-nk)+e(t)$$

e(t): residual difference (i.e., the difference between the expected value and the measured value)
nk: time delay from the commonly used ideal blood velocity waveform that corresponds to the ECG waveform $$A(q)=1+a_1q^{-1}+\ldots+a_{na}q^{-na}$$

$$B(q)=b_1+b_2q^{-1}+\ldots+b_{nb}q^{-nb+1}$$

(A(q) and B(q) are irreducible polynomials of shift operator q) na, nb, nk: integer arguments Therefore, in the memory part 7, a coefficient in the model of the commonly used ideal blood velocity waveform as shown below is preliminarily stored for each classified group.

$$a_i=(a_1,a_2,\ldots,a_{na}), b_j=(b_1,b_2,\ldots,b_{nb})$$

The waveform estimation part 93 estimates the ideal blood velocity waveform for a patient whose blood velocity is currently being measured. This measurement is based on: the measured blood velocity waveform Vp(t) (received from the measured waveform calculation part 91); the ECG waveform u(t) (received from the ECG waveform acquisition part 92); and the coefficient $a_i=(a_1, a_2, \ldots, a_{na})$, $b_j=(b_1, b_2, \ldots, b_{nb})$ stored in the memory part 7. At this time, it is determined which of the above-mentioned groups the patient belongs to, and a coefficient that corresponds to the group is used for the coefficient that is used for the estimation. This estimated waveform is called an estimated waveform ye(t) as described below. This estimated waveform ye(t) can be expressed as follows.

$$ye(t)=-\Sigma\{a_i*V_p(t-i)\}+\Sigma\{b_j*u(t-j)\}$$

The waveform estimation part 95 transmits the estimated waveform ye(t) to the interpolation part 94.

The interpolation part 94 stores the threshold for differences between the measured blood velocity waveform Vp(t) and the estimated waveform ye(t). Here, this threshold is a value indicating that the measured blood velocity waveform Vp(t) is affected by valve signals at that time when the threshold is exceeded by the difference between the measured blood velocity waveform Vp(t) and the estimated waveform ye(t). Therefore, the purpose of this threshold is to exclude the effects of high-speed valve signals, and if approximation to the estimated waveform is strongly requested, almost all values are excluded. Thus, it is preferable to set this threshold according to any requests on how much range should be left as the range of excluded effects of valve signals and a range of the measured blood velocity waveform Vp(t) after excluding the effects of valve signals. Moreover, the interpolation part 94 calculates the difference between the measured blood velocity waveform Vp(t) and the estimated waveform ye(t) in the patient whose received present blood velocity is being measured and determines parts where the difference exceeds the threshold.

In the present embodiment, a threshold is given for both positive and negative sides. However, this threshold may be set using another method. For example, because the value is higher in parts with the effects of valves compared to the estimated waveform, the threshold value may be set only on the positive side when the estimated waveform is subtracted from the measured blood velocity waveform. Moreover, when the measured blood velocity waveform is subtracted from the estimated waveform, the threshold value may be set only on the negative side. Furthermore, the absolute value of the difference between the measured blood velocity waveform and the estimated waveform may be used to set the threshold for the absolute value.

The interpolation part 94 excludes parts exceeding the threshold from the measured blood velocity waveform Vp(t) of the patient whose blood velocity is currently being measured.

Furthermore, the interpolation part 94 plugs the estimated waveform ye(t) into the excluded parts of the measured blood velocity waveform Vp(t). Moreover, the interpolation part 94 interpolates the gap between the estimated waveform ye(t) and the measured blood velocity waveform Vp(t). The method for this interpolation is not limited to any particular kind, and any methods may be used, including linear interpolation, spline interpolation, or interpolation with a linear prediction using the peak of the measured blood velocity waveform. Moreover, in the present embodiment, interpolation is conducted after plugging the estimated waveform ye(t) into the excluded parts, but the excluded parts of the measured blood velocity waveform Vp(t) may be directly interpolated without plugging the estimated waveform ye(t). The method for this interpolation is also not limited to any particular kind, and any methods may be used, including linear interpolation, spline interpolation, or interpolation with a linear prediction using the peak of the measured blood velocity waveform. At this time, because the process of linear interpolation is simple, the burden applied to the interpolation part 94 is small. On the other hand, with spline interpolation and a method of interpolating with a linear prediction using the peak of the measured blood velocity waveform, the processes are complicated but interpolation can be conducted with a smooth curve, and thus a waveform that is closer to the actual waveform can be created. Furthermore, spline interpolation is effective when the interval for interpolation is short, but with the interpolation method of a linear prediction using the peak of the measured blood velocity waveform, interpolation can be conducted even when the interval for interpolation is long. The blood velocity waveform created by this interpolation part 94 is called the "waveform for range setup" as described below.

The interpolation part 94 transmits the waveform for range setup to the velocity range setup part 95.

The velocity range setup part 95 conducts statistical computing to calculate the upper limit and the lower limit of the velocity range. Here, statistical computing includes a normal distribution model in which: a histogram is created from the waveform for range setup to calculate the velocity distribution; the mean and the variance are calculated from the distribution of the waveform for range setup that has been weighted based on the velocity distribution; the mean±coefficient×σ becomes estimate values for the upper and lower limits of the velocity range; and a post-smoothing threshold processing model in which values that correspond to the coefficient % of the peak value become the upper and lower limits of the velocity range according to the distribution of the weighted waveform for range setup, etc. The method of calculating this velocity range is described in detail in Japanese published unexamined application No. 2005-185731.

Subsequently, the velocity range setup part 95 calculates the repetition frequency (PRF) that corresponds to the set velocity range.

Moreover, the velocity range setup part 95 calculates the maximum velocity range from the maximum value on the upper side (positive side) from the current reference position (baseline) and the minimum velocity range from the maximum value on the lower side (negative side) using the waveform for range setup and compares the maximum velocity range with the minimum velocity range to calculate the displacement of the baseline (reference position). For example, if the mean value of the maximum velocity range and the minimum velocity range is placed in the center of the screen, the shift amount is calculated by obtaining the distance between the mean value and the baseline (=0). The velocity offset (BLS), which is the displacement of the reference position (baseline), is calculated.

The method of calculating this velocity offset (BLS) is described in detail in Japanese published unexamined application No. 2005-185731.

As described above, once the repetition frequency (PRF) and the velocity offset (BLS) are decided, the velocity range setup part 95 outputs the repetition frequency (PRF) to the transceiving part 3. Moreover, the velocity range setup part 95 simultaneously outputs the velocity offset (BLS) to the FFT calculation part 54 of the Doppler signal-processing part 5.

Additionally, in the present embodiment, the auto range/auto BLS-processing part 9 may be constituted as hardware or software. For example, by constituting the auto range/auto BLS-processing part 9 using a CPU and executing a program by reading the program from a memory area (not shown), the functions of the measured waveform calculation part 91, the ECG waveform acquisition part 92, the waveform estimation part 93, the interpolation part 94, and the velocity range setup part 95 may be executed.

At this time, in the present embodiment, adjustments of the velocity offset and the velocity range are both made, but the ultrasonic imaging apparatus of the present invention is operable only by the adjustment of the velocity range. In that case, the offset is not displaced and always has 0 Hz as a reference, but a Doppler spectrum image with the velocity range adjusted and the folding reduced can be obtained.

(Actions)

Figure 3:
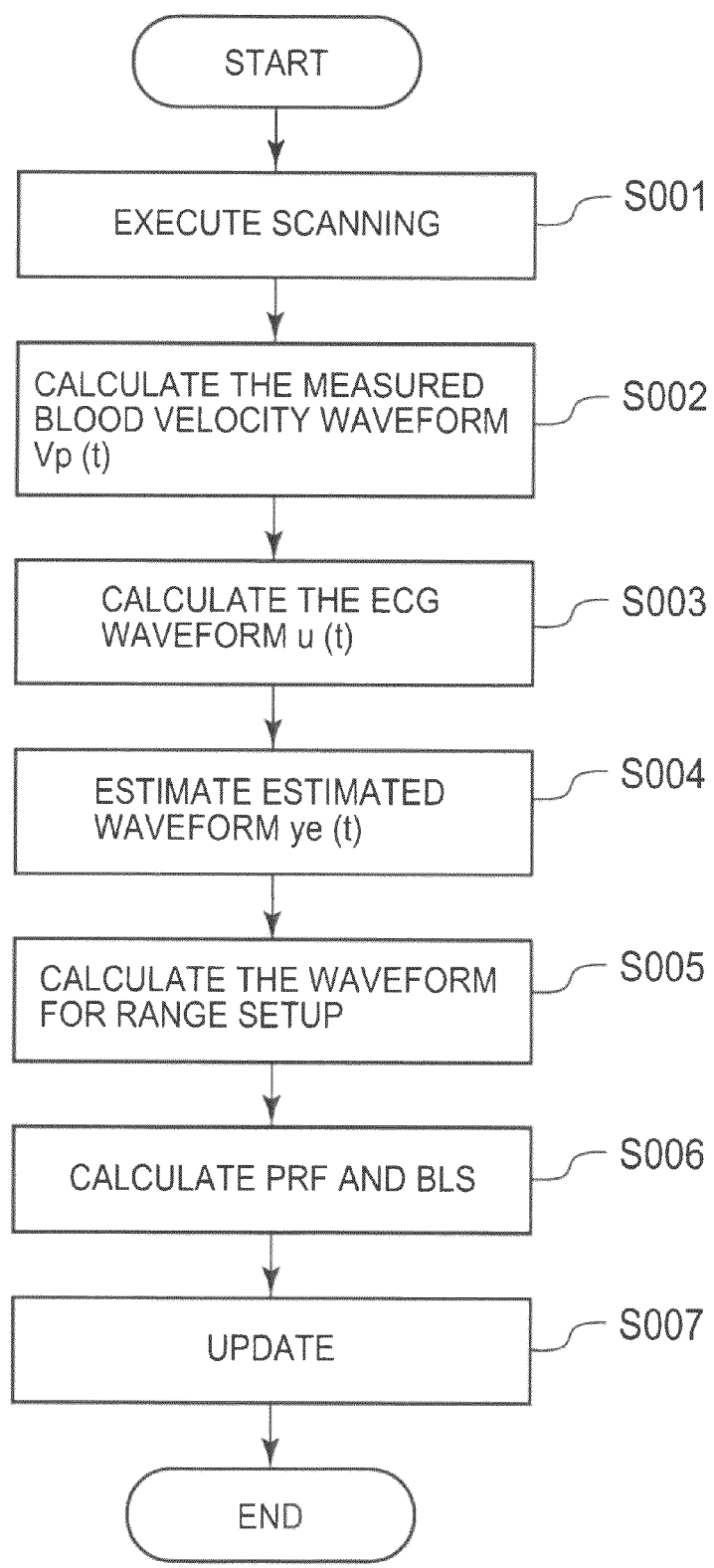
FIG. 3 is a diagram of a flowchart illustrating a sequence of actions of an ultrasonic imaging apparatus related to Embodiment 1.

A sequence of actions of the ultrasonic imaging apparatus related to Embodiment 1 of this invention will now be described with reference to FIG. 3. FIG. 3 is a diagram of a flow chart illustrating a sequence of actions of the ultrasonic imaging apparatus related to Embodiment 1 of this invention.

(Step S001)

Firstly, ultrasound is transmitted to the body to be examined and a B-mode cross-sectional image and a Doppler spectrum image are generated based on the reflected waves from the body to be examined. The Doppler waveform data generated in the FFT calculation part 54 is output from the FFT calculation part 54 to the display part 8 via the DSC 6 and displayed on the display part 8 along with the B-mode cross-sectional image. Furthermore, the Doppler waveform data is output from the FFT calculation part 54 to the auto trace part 7.

(Step S002)

Once the Doppler waveform is acquired in Step S001, the measured waveform calculation part 91 traces a marginal region of the Doppler spectrum image (maximum velocity Vp) in the direction of that time to detect the blood velocity waveform of the maximum velocity Vp. Furthermore, the measured waveform calculation part 91 calculates the measured blood velocity waveform Vp(t), which is a function that indicates the blood velocity waveform of the maximum velocity Vp. The measured waveform calculation part 91 then outputs the measured blood velocity waveform Vp(t) to the waveform estimation part 93 and the interpolation part 94.

(Step S003)

In Step S003, the ECG waveform acquisition part 92 traces the maximum amplitude of a signal received from the electrocardiograph 10 and calculates the ECG waveform u(t), which is a function that indicates the traced waveform. The ECG waveform acquisition part 92 then outputs the ECG waveform u(t) to the waveform estimation part 93.

(Step S004)

In Step S004, the waveform estimation part 93 estimates the ideal blood velocity waveform (estimated waveform ye(t)) of a patient whose blood velocity is currently being measured. This estimation is based on the measured blood velocity waveform Vp(t), ECG waveform u(t), and a coefficient of a model of a commonly used ideal blood velocity waveform preliminarily stored in the memory part 7. The waveform estimation part 93 then outputs the estimated waveform ye(t) to the interpolation part 94.

(Step S005)

The interpolation part 94 calculates the difference between the measured blood velocity waveform Vp(t) and the estimated waveform ye(t), excludes excess parts of the difference over the stored threshold from the measured blood velocity waveform Vp(t), and interpolates the excluded parts in order to calculate the waveform for range setup.

(Step S006)

The velocity range setup part 95 conducts a statistical calculation process based on the waveform for range setup to calculate the repetition frequency (PRF) and velocity offset (BLS).

(Step S007)

As described above, once the repetition frequency (PRF) and the velocity offset (BLS) are determined, the velocity range setup part 95 outputs the repetition frequency (PRF) to the transceiving part 3. At the same time, the velocity range setup part 95 outputs the velocity offset (BLS) to the FFT calculation part 54 in the Doppler signal-processing part 5. The transceiving part 3 transmits and receives ultrasound to and from the ultrasonic probe 2 according to the repetition frequency (PRF) calculated by the velocity range setup part 95. Moreover, according to the velocity offset (BLS) calculated by the velocity range setup part 95, the FFT calculation part 54 changes the read address of the FFT process by the shift amount to adjust the velocity offset. Thereby, the velocity range and the velocity offset (BLS) are updated.

As described above, according to the ultrasonic imaging apparatus 1 related to this embodiment, the velocity range and the velocity offset of the blood velocity waveform with the effects of valve signals excluded based on the Doppler spectrum image acquired by scanning are obtained automatically. Moreover, by using the velocity range and the velocity offset, the Doppler velocity range, etc. can be changed following shifts in the state of the blood flow.

(Example)

With reference to FIG. 4A-D, the display of a blood velocity waveform will be described below. For this purpose, an example of a blood velocity waveform with the effects of valve signals excluded by using the ultrasonic imaging apparatus related to the present embodiment is used, along with a comparative example of a blood velocity waveform formed with a conventional method without using the ultrasonic imaging apparatus related to the present embodiment.

FIG. 4A is a diagram of a graph for calculating the blood velocity waveform using the ultrasonic imaging apparatus related to the present invention. FIG. 4B is a graph in which the velocity range of the blood velocity waveform has been set up manually in a conventional ultrasonic imaging apparatus. FIG. 4C is a graph that shows an ideal velocity range of the blood velocity waveform in the present example. FIG. 4D is a graph in which the velocity range of the blood velocity waveform has been set up using the ultrasonic imaging apparatus related to the present embodiment. Each graph of FIG. 4 is a graph that shows the velocity range (kHz) in the vertical axis and time (sec.) in the horizontal axis.

The graph 501 shown in FIG. 4A is a graph that shows the measured blood velocity waveform Vp(t) before the effects of valves have been excluded; the graph 502 is a graph that shows the estimated waveform ye(t); the graph 503 is a graph that shows the ECG waveform ECG(t) that corresponds to the blood velocity waveform of the graph 501; and the graph 504 is a graph that shows the blood velocity waveform with the effects of valves excluded using the ultrasonic imaging apparatus related to the present embodiment.

In the example, firstly, the measured blood velocity waveform Vp(t) shown in the graph 501 is created by conducting a Doppler automatic trace for a measured Doppler signal. Then, the estimated waveform ye(t) shown in the graph 502 is created using the ECG waveform ECG(t) shown in the graph 503 and the ideal blood velocity waveform that has been statistically calculated. Subsequently, excess parts of the difference between this estimated waveform ye(t) and the measured blood velocity waveform Vp(t) over the threshold, are excluded and interpolated, thus creating the blood velocity waveform with the effects of valves excluded shown in the graph 504.

At this time, if the blood velocity waveform is displayed without excluding the effects of valves from the measured waveform Vp(t), the velocity range is required to be 5.6 (kHz). On the other hand, if the effects of valves is excluded by manual operation from the measured waveform Vp(t) according to the relevant art, it is possible to have a velocity range of 3.9 (kHz) as shown in FIG. 4B. However, if the velocity range is calculated based on an ideal waveform statistically calculated considering minimization of the effects of valves, it is ideal to have a velocity range of 3.2 (kHz) for the blood velocity waveform in the present example. Therefore, if the blood velocity waveform with the effects of valves excluded shown in the graph 504 is used using the ultrasonic imaging apparatus related to the present embodiment, it is possible to have the velocity range of 3.2 (kHz) as shown in FIG. 4D.

As described above, while it is difficult to obtain an ideal velocity range using manual operation, it is possible to obtain a velocity range near the ideal velocity range by excluding the effects of valves using the ultrasonic imaging apparatus of the present embodiment.

Figure 5:
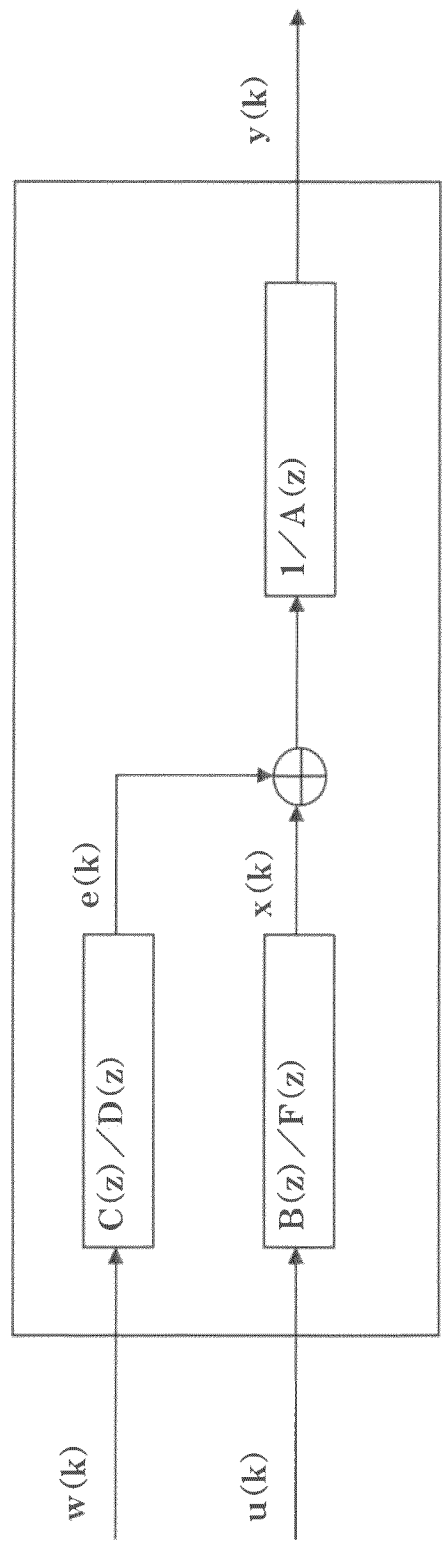
FIG. 5 is a diagram illustrating a parametric model for system identification.

Here in the present embodiment, the ARX model is used for system identification, but other mathematical models may be used if they are parametric models for system identification (for example, refer to "advanced system identification for control" by Shuichi Adachi, Tokyo Denki University). This parametric model includes an FIR (Finite Impulse Response) model, an ARMAX (Auto Regressive Moving Average eXogenous) model, an OE (Output Error) model, and a BJ (Box and Jenkins) model, as well as the ARX model and other models. The parametric model for system identification is expressed as shown in FIG. 5. FIG. 5 is a diagram showing the parametric model for system identification. In FIG. 5, $A(z)*y(k)=\{B(z)/F(z)\}*u(k)+\{C(z)/D(z)\}*w(k)$.

$$A(z)=1+a_1*z_{-1}+\ldots+a_n*z_{-n}$$

$$B(z)=b_1*z_{-1}+b_2*z_{-2}+\ldots+b_m*z_{-m}$$

$$C(z)=c_1*z_{-1}+c_2*z_{-2}+\ldots+c_p*z_{-p}$$

$$D(z)=1+d_1*z_{-1}+d_2*z_{-2}+\ldots+d_q*z_{-q}$$

$$F(z)=1+f_1*z_{-1}+f_2*z_{-2}+\ldots+f_r*z_{-r}$$

Moreover, the parametric model for system identification is expressed as follows.

$$e(k)+d_1*e(k-1)+\ldots+d_q*e(k-q)=c_1*w(k-1)+c_2*w(k-2)+c_p*w(k-p)$$

$$x(k)+f_1*x(k-1)+\ldots+f_q*x(k-q)=b_1*u(k-1)+b_2*u(k-2)+b_m*w(k-m)$$

$$y(k)+a_1*y(k-1)+\ldots+a_q*y(k-q)=e(k)+x(k)$$

Moreover, in the present embodiment, the velocity range is adjusted after the interpolation, but only the interpolated blood velocity waveform with the effects of valves excluded may be created. With this configuration, the blood velocity waveform with the effects of valves excluded can be acquired, facilitating the measurement of blood flow amount and improving the accuracy of measurement.

Furthermore, the velocity range may be adjusted by using the blood velocity waveform with the effects of valves excluded without interpolation. In this case, the velocity range setup part 95 stores the threshold. The velocity range setup part 95 then compares the estimated waveform with the measured blood velocity waveform to calculate parts that exceed the threshold. With this configuration, the accuracy of the velocity range adjustment decreases by a few %, but because the calculation becomes simple, the speed of calculating the velocity range can be improved.

[Embodiment 2]

Figure 6:
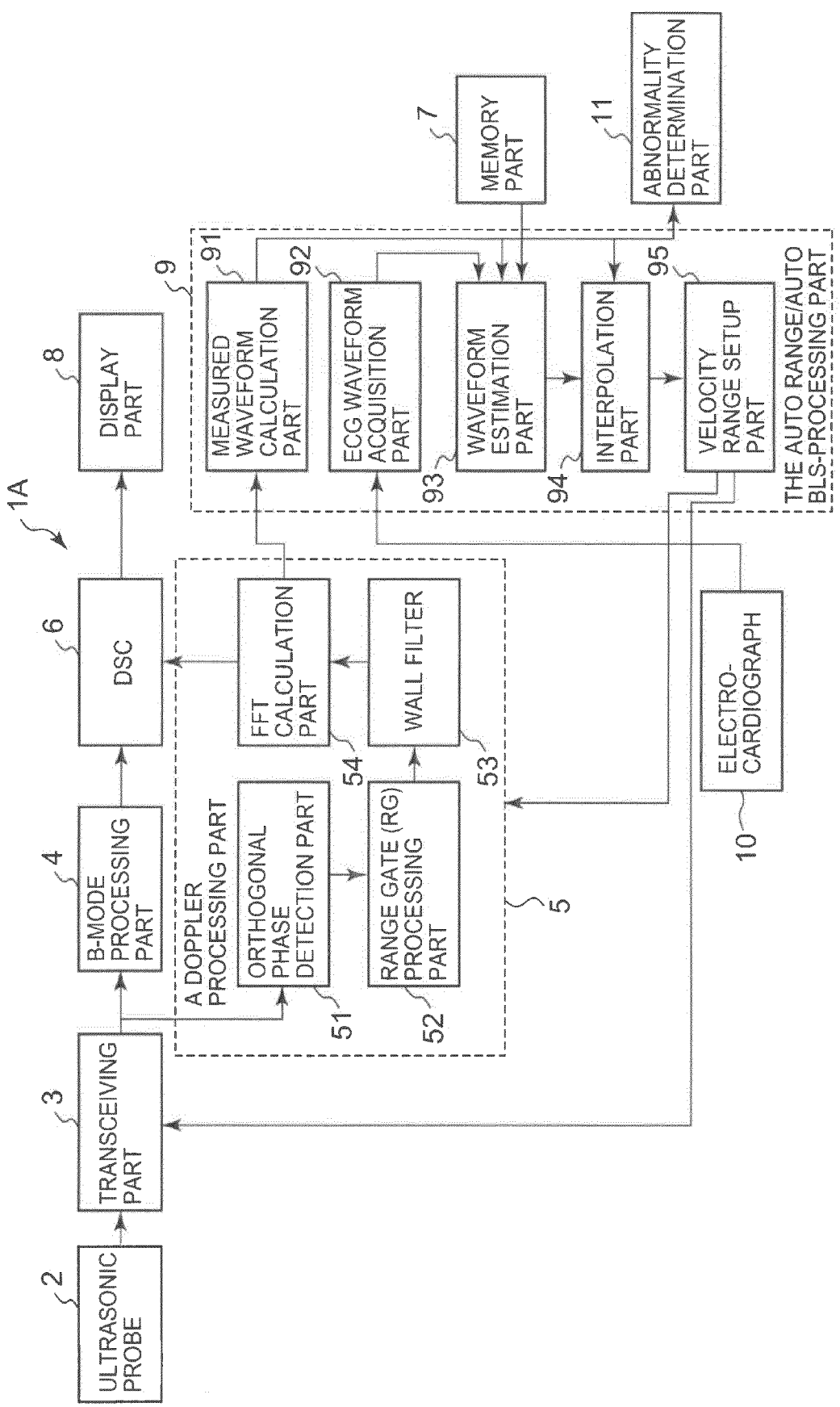
FIG. 6 is a block diagram of an ultrasonic imaging apparatus related to Embodiment 2.

Next, an ultrasonic imaging apparatus related to Embodiment 2 of this invention will be described. The ultrasonic imaging apparatus 1A related to Embodiment 2 further comprises an abnormality determination part 11 in addition to the ultrasonic imaging apparatus 1 related to Embodiment 1. FIG. 6 is a block diagram illustrating the functions of the ultrasonic imaging apparatus related to Embodiment 2. The determination of an abnormality in the ultrasonic imaging apparatus 1A is described below.

An abnormality determination part 11 creates a state space based on individual ideal blood velocity waveforms with no effects of valve signals for each age and disorder stored in the memory part 7 as statistical data. At this time, the state space is a space that includes blood velocity waveforms that can be considered as being in a normal state.

The abnormality determination part 11 acquires a measured blood velocity waveform Vp(t) from the measured waveform calculation part 91.

The abnormality determination part 11 selects a corresponding state space based on the age and disorder of the patient with the blood velocity waveform Vp(t) and calculates the Mahalanobis' generalized distance between the state space and the blood velocity waveform Vp(t). At this time, the Mahalanobis' generalized distance is an index using the correlation between variables and is a distance scale that indicates the distance from the target reference space.

The abnormality determination part 11 determines that the blood velocity is abnormal when the calculated Mahalanobis' generalized distance exceeds the pre-stored threshold for the Mahalanobis' generalized distance. The abnormality determination part 11 then notifies the operator that the blood velocity is abnormal using the display part 8, etc.

Thereby, any abnormality in blood velocity that exceeds the threshold is automatically reported to the operator, and thus oversights of abnormalities in blood velocity can be reduced and a faster and more accurate diagnosis can be provided for a patient.

What is claimed is:

1. An ultrasonic imaging apparatus comprising:
a transceiving part configured to transmit and receive ultrasound with a repetition frequency that corresponds to a velocity range indicating the measurable velocity, to and from a diagnostic site that contains a moving fluid within a body to be examined;
a Doppler signal-processing part configured to generate a Doppler spectrum image that shows the velocity of said moving fluid based on signals obtained from the transmission and reception of said ultrasound;
a memory part configured to preliminarily store a modeled value based on a model that correlates a standard blood velocity waveform with an ECG waveform;
a measured waveform calculation part configured to calculate a measured blood velocity waveform based on said spectrum image of a specified patient, which measured blood velocity waveform includes a valve signal;
an ECG waveform acquisition part configured to acquire an ECG waveform at a timing corresponding to said measured blood velocity waveform;
a waveform estimation part configured to estimate a blood velocity waveform of said specified patient based on said specified patients measured blood velocity waveform, said ECG waveform, and said modeled value, the estimated blood velocity waveform being free from a valve signal; and
an interpolator configured to exclude a portion of the measured blood velocity waveform where a difference between the measured blood velocity waveform and the estimated blood velocity waveform exceeds a predetermined threshold for judgement of an influence by a valve signal, and to replace the excluded portion of the measured blood velocity waveform with the estimated blood velocity waveform for interpolation of the difference between the measured blood velocity waveform and the estimated blood velocity waveform.

2. An ultrasonic imaging apparatus according to claim 1, wherein said standard blood velocity waveform is a blood velocity waveform that is not affected by valve signals.

3. An ultrasonic imaging apparatus according to claim 1, wherein
a model of said standard blood velocity waveform is a model for a parametric model for system identification, and said modeled value is a coefficient calculated by conducting system identification using a parametric model for said system identification.

4. An ultrasonic imaging apparatus according to claim 1, wherein
said interpolation part is configured to conduct said interpolation using either linear interpolation, spline interpolation, or interpolation with a linear prediction using a peak of said measured blood velocity waveform.

5. A method of acquiring ultrasonic images comprising:
transmitting and receiving ultrasound with a repetition frequency that corresponds to a velocity range indicating the measurable velocity, to and from a diagnostic site that contains a moving fluid within a body to be examined;
generating a Doppler spectrum image that shows the velocity of said moving fluid based on signals obtained from the transmission and reception of said ultrasound;
preliminarily storing a modeled value based on a model that correlates a standard blood velocity waveform with an ECG waveform;
calculating a measured blood velocity waveform based on said spectrum image of a specified patient, which measured blood velocity waveform includes a valve signal;
acquiring an ECG waveform at a timing corresponding to said measured blood velocity waveform;
estimating a blood velocity waveform of said patient based on said measured blood velocity waveform, said ECG waveform, and said modeled value, the estimated blood velocity waveform being free from a valve signal; and
excluding a portion of the measured blood velocity waveform where a difference between the measured blood velocity waveform and the estimated blood velocity waveform exceeds a predetermined threshold for judgement of an influence by a valve signal, and replacing the excluded portion of the measured blood velocity waveform with the estimated blood velocity waveform for interpolation of the difference between the measured blood velocity waveform and the estimated blood velocity waveform.

6. A method of acquiring ultrasonic images according to claim 5, wherein
a model of said standard blood velocity waveform is a model for a parametric model for system identification, and said modeled value is a coefficient calculated by conducting system identification using a parametric model for said system identification.

7. A method of acquiring ultrasonic images according to claim 5, wherein
said interpolation comprises conducting said interpolation using either linear interpolation, spline interpolation, or interpolation with a linear prediction using a peak of said measured blood velocity waveform.

* * * * *